United States Patent
Kurth

(10) Patent No.: US 8,409,299 B2
(45) Date of Patent: Apr. 2, 2013

(54) LIMB STUMP RECEIVING SLEEVE COMPRISING AN INTEGRATED LOCKING DEVICE FOR A SEALING ELEMENT

(75) Inventor: Christof Kurth, Heinersreuth (DE)

(73) Assignee: Medi GmbH & Co. KG, Bayreuth (DE)

( * ) Notice: Subject to any disclaimer, the term of this patent is extended or adjusted under 35 U.S.C. 154(b) by 212 days.

(21) Appl. No.: 12/936,350

(22) PCT Filed: Apr. 2, 2009

(86) PCT No.: PCT/DE2009/000425
§ 371 (c)(1),
(2), (4) Date: Nov. 2, 2010

(87) PCT Pub. No.: WO2009/121340
PCT Pub. Date: Oct. 8, 2009

(65) Prior Publication Data
US 2011/0112656 A1    May 12, 2011

(30) Foreign Application Priority Data

Apr. 5, 2008   (DE) .................... 20 2008 004 714 U
Apr. 26, 2008  (DE) .......................... 10 2008 021 054

(51) Int. Cl.
*A61F 2/80* (2006.01)
(52) U.S. Cl. ......................................................... 623/34

(58) Field of Classification Search ................... 623/33, 623/34, 36, 37; 601/6, 9–11
See application file for complete search history.

(56) References Cited

U.S. PATENT DOCUMENTS
5,688,225 A * 11/1997 Walker ........................... 601/11

FOREIGN PATENT DOCUMENTS

| DE | 20 60 239 A | 6/1992 |
|---|---|---|
| DE | 101 42 492 A1 | 4/2003 |
| EP | 0 631 765 AY | 1/1995 |
| EP | 1 875 882 XY | 1/2008 |
| JP | 07-051306 | 2/1995 |
| JP | 2002-291781 A * | 10/2002 |
| JP | 2002291781 A | 10/2002 |
| JP | 2005501687 | 1/2005 |
| WO | 03/024370 Y | 3/2003 |

* cited by examiner

Primary Examiner — David H. Willse
(74) Attorney, Agent, or Firm — Lucas & Mercanti, LLP

(57) ABSTRACT

The invention relates to a limb stump receiving sleeve (1) comprising an integrated locking device for locking a limb by sealing a distal region of the interior of the stump receiving sleeve in relation to the limb and the surrounding atmosphere, a functional element (3) of the device being integrated into the inner face of the receiving sleeve and a sealing element (5) that extends inwards being reversibly attachable to the functional element in a positive fit, preventing air from flowing in behind said element.

9 Claims, 4 Drawing Sheets

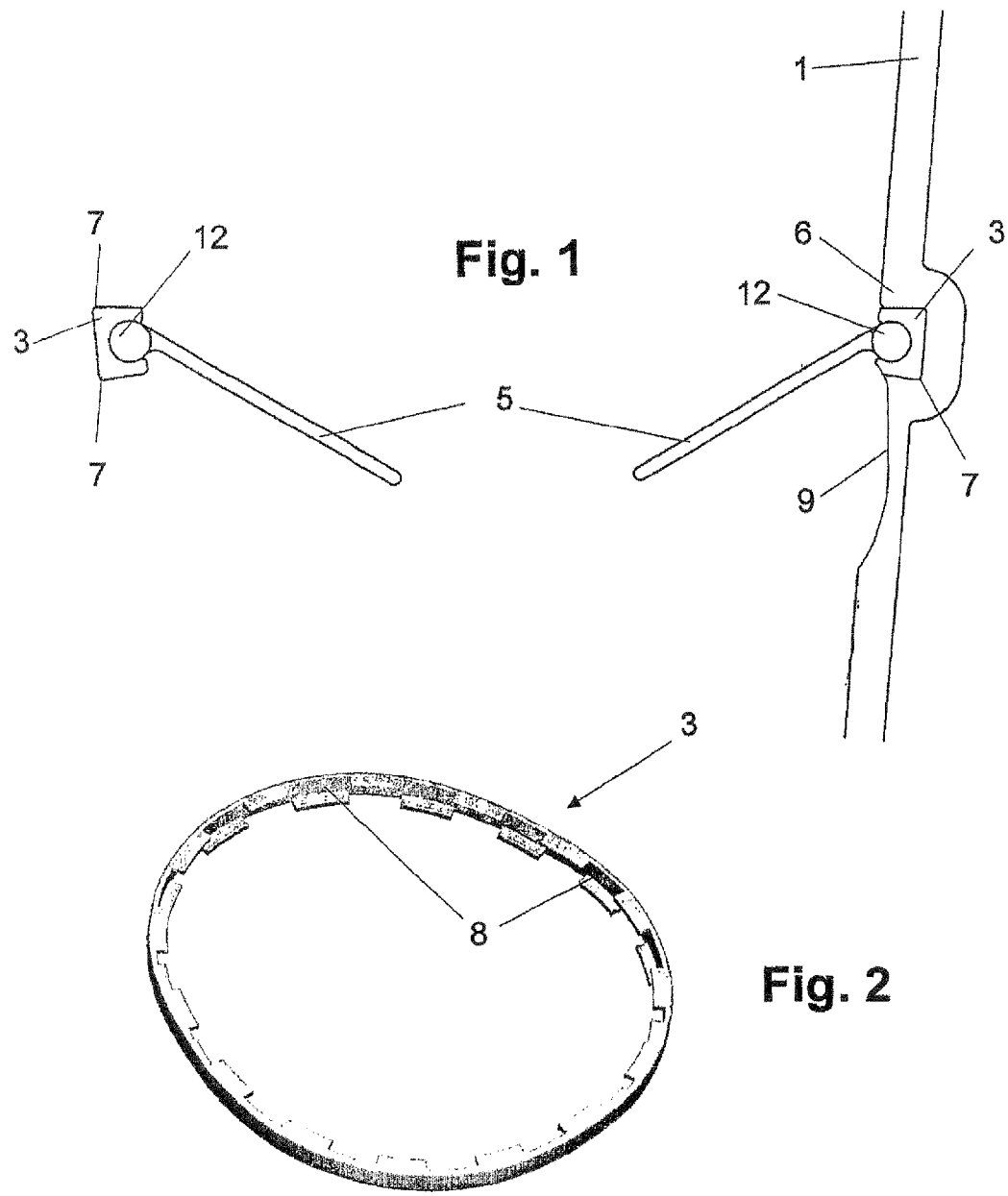

LIMB STUMP RECEIVING SLEEVE COMPRISING AN INTEGRATED LOCKING DEVICE FOR A SEALING ELEMENT

This application is a 371 of PCT/DE2009/000425 filed Apr. 2, 2009, which in turn claims the priority of DE 20 2008 004 714.5 filed Apr. 5, 2008 and DE 10 2008 021 054.4 filed Apr. 26, 2008, the priority of these applications is hereby claimed and these applications are incorporated by reference herein.

BACKGROUND OF THE INVENTION

The present invention relates to a limb stump receiving sleeve comprising an integratable or integrated receptacle for a sealing element, by means of which a limb stump is locked in a stump receiving sleeve by sealing the distal region of the interior of the stump receiving sleeve with respect to the limb stump and the surrounding atmosphere.

When connecting a patient's stump to a limb stump receiving sleeve, the stump, which is covered by a liner, is usually inserted and fixed from above, in the direction of the closed, distal end of the stump receiving sleeve.

The stump is fixed by a negative pressure produced in the limb stump receiving sleeve when inserting the stump, and for this purpose numerous stump receiving sleeves have a valve close to their distal end, via which the compressed air can escape from the sleeve during insertion of the stump.

In many embodiments, the liner is sealed with respect to the receiving sleeve only by sealing resulting from planar bearing contact between these two parts themselves, and the sealing is dependent on the materials used and the dimensioning of the liner and of the interior of the stump receiving sleeve. If the external diameter of the liner at least corresponds to the internal diameter of the shaft, negative pressure can be produced permanently in the shaft via this form of the planar seal. If the external diameter of the limb stump, including the liner, is greater than the internal diameter of the shaft, however, the resultant pressure on the shaft will feel unpleasant, or it will be harder to fit into the prosthesis. Since fluctuations in stump volume can be observed in most prosthesis wearers, the resultant fit between the receiving sleeve and the liner varies.

Furthermore, when the stump is moved, i.e. when walking, a gap may briefly appear between the stump and the inner side of the receiving sleeve, through which gap the internal pressure escapes and the fit of the stump in the receiving sleeve is impaired. This is all the more so if, owing to a desired wearing comfort, the fit of the stump with respect to the receiving sleeve is no longer so pronounced. This often results in the stump sliding out of the stump receiving sleeve when the limb is lifted.

In order to solve this problem, EP 0 631 765 B1 proposes a stump receiving device into which a sealing element is inserted, said sealing element having a virtually circular design and having an opening in the center, through which the stump is inserted into the receiving sleeve. A seal is thereby continuously provided, even when the stump is moved, in the receptacle between said sealing membrane and the liner or stump itself.

The sealing element described is circumferentially provided with a ring which engages into a groove made in the stump receiving sleeve, where it is fixed.

These embodiments have the disadvantage that firstly the sealing in the groove, into which the ring of the sealing element engages, is problematic or can only be implemented with a high level of expenditure, and secondly the positive locking of the ring in the groove is often insufficient.

When fitting the stump into or removing it from the stump receiving sleeve, the circumferential ring is often pulled out of the groove, as a result of which naturally either the function is not performed or the sealing element has to be laboriously fitted back in. Furthermore, it is very complicated to implement the circumferential groove such that it is formed in a positively locking manner and free from bubbles on the inner side of the limb stump receiving sleeve.

SUMMARY OF THE INVENTION

It is an object of the present invention to provide a limb stump receiving sleeve comprising an integrated receptacle for a sealing element, into which a patient's stump can easily be inserted and in which the stump is fitted well, reliably and securely by a negative pressure produced in the distal region of the stump receiving sleeve.

The invention proposes a limb stump receiving sleeve comprising an integratable receptacle for an inwardly extending sealing element, which can be reversibly attached in a positively locking manner and in such a way that air cannot flow in behind it.

This ensures that a limb stump is locked by sealing a distal region in the interior of the stump receiving sleeve with respect to the limb stump and the surrounding atmosphere.

The stump receiving sleeve equipped with the receptacle according to the invention and the associated sealing element preferably also has a valve in its distal region under the sealing device.

When fitting the stump into the receiving sleeve, the stump is inserted through the sealing element into the sleeve, and the air compressed in the process can escape outward through the valve. The preferred embodiment of the valve prevents air from being able to flow from outside into the distal region of the stump receiving sleeve without the valve being opened, and therefore the negative pressure produced by tensile force when an attempt is made to pull the stump out of the sleeve is maintained and fixes the stump in the receiving sleeve.

The functional element, to which the sealing element can be attached, is preferably fixed non-releasably and in such a way that air cannot flow in behind it in a groove, preferably a circumferential groove, which is present on the inner side of the receiving sleeve, where in this respect the functional element can be enclosed, pressed in, adhesively bonded in, molded or, for example, even vulcanized in.

The functional part is preferably made of an elastic or at least partially elastic material and has good sealing properties. According to a further embodiment according to the invention, the functional element has an undercut, or widens to the rear like a trapezoid, which engages into a corresponding groove in the receiving sleeve, and whereby a firm fit in the groove with corresponding sealing is achieved.

The functional element, which is fixed in the groove in the stump receiving sleeve and to which an inwardly extending sealing element with a preferably central, preferably tri-oval or oval or else circular opening can be attached, thus forms a circumferential, annular receptacle in the interior of the stump receiving sleeve.

That side of this receptacle which faces toward the interior of the stump receiving sleeve is preferably provided with a circumferential groove, in which in turn the sealing element can be reversibly attached in a positively locking manner and in such a way that air cannot flow in behind it.

A substantially rigid, circumferential ring which can be matched to the form of the stump is used to attach the sealing element in the described circumferential groove in the functional element in a positively locking manner and in such a way that air cannot flow in behind it.

This preferred embodiment produces a sealing connection between the functional part and the sealing element, where the sealing element rests on the stump when the stump is being fitted into the receiving sleeve, and seals it circumferentially with respect to the outer atmosphere. The pressure produced in the distal region of the receiving sleeve, under the ring of the functional element, can escape through the valve, and the negative pressure which has been described when the stump is pulled out is produced in the interior of the receiving sleeve, as a result of which the stump is fixed.

When the stump is being fitted, the sealing element, which nestles around the stump or liner, is pulled together with the stump in the direction of the distal end of the stump sleeve, where it rests circumferentially between the stump and the inner wall of the stump sleeve. A recess or taper is provided on the inner side of the receiving sleeve distally from the circumferential functional element, and the sealing membrane and, in particular, the transition between the membrane and circumferential ring can retract into said recess or taper after the fitting operation, so that in this region no additional circularly acting pressure, which would be physiologically disadvantageous, is built up on the stump.

The circumferential functional element itself, in which the sealing element is fixed in the groove, also has a recess at its distal end in the groove in the stump receiving sleeve, i.e. has a smaller diameter at this point in the groove, in order to provide space in this region for the sealing element, which deforms when the amputee is fitted into the sleeve.

Before the stump of an amputee, which is usually covered with a liner, is fitted into the sleeve, the stump receiving sleeve should be provided with the sealing element, which is connected in a positively locking manner with its circumferential, harder edge, which is non-releasably connected to the sealing membrane, in the groove in the functional element fixed in the interior of the stump receptacle.

The sealing membrane itself is preferably made of an elastomer material and has, substantially in the center, a substantially tri-oval or oval or else circular opening, through which the limb stump is inserted into the stump receiving sleeve. The materials of the sealing membrane are preferably chosen in such a way as to prevent adhesion of the sealing part or of the sealing membrane to the liners used.

The clamping ring extending around the sealing membrane is designed in terms of material and size such that it can be simply inserted into the sleeve by twisting and can be attached in the groove at that side of the functional part which faces toward the inner side of the receiving sleeve, where it forms a positively locking and sealing connection with respect to the circumferential functional element ring.

This connection has such a positive lock that it withstands the tension exerted on the sealing element when the stump is being fitted into and removed from the receiving sleeve without any problem and without allowing air to flow in behind it, thereby avoiding the unpleasant formation of folds or protrusions, which could press against the stump in the region of the seal.

As mentioned, the stump is fixed in the limb stump receiving sleeve by the negative pressure produced in the distal region of the receiving sleeve. The volumetric compartment described can preferably be rear-ventilated again by a valve integrated in the shaft, in order to make it possible for the patient to pull the stump back out of the receiving sleeve, where in this respect it is possible to use a plurality of valves or else valves which can be closed in a different direction of flow, or else direction-changing valves.

The invention is described in more detail below, by way of example, with reference to drawings.

BRIEF DESCRIPTION OF THE DRAWINGS

FIG. 1 is an illustration of the sealing element attached in the functional element, which is inserted into the receiving sleeve.

FIG. 2 is a perspective illustration of a functional element.

DETAILED DESCRIPTION OF THE INVENTION

In practice, FIG. 1 shows an excerpt of a section through a receiving sleeve 1 and through a complete device 4, although the receiving sleeve has been omitted on the left-hand side. A groove 6, which is provided with an undercut, as can be seen, and into which the functional element 3 of the overall device 4 is inserted, preferably permanently, is incorporated in the receiving sleeve 1. For a better fit in the groove 6 in the receiving sleeve 1, the functional element 3 has a dovetail which corresponds to the undercut in the receiving sleeve 1, and is also fixed permanently and reliably by suitable measures, such as bonding in or encapsulation.

Figure 3:
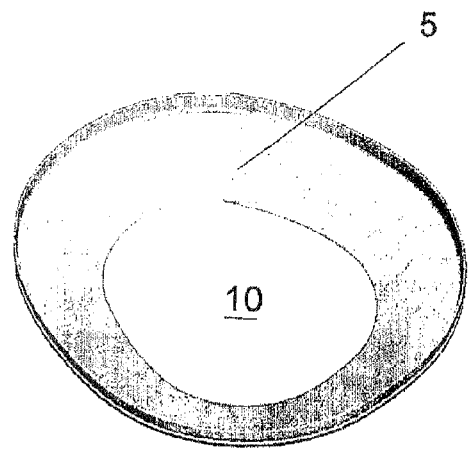
FIG. 3 is a perspective illustration of a sealing element.

As can readily be seen in FIG. 2, the functional element 3, which is fixed circumferentially in the receiving sleeve 1, for its part likewise has a circumferential groove 8, in which the sealing element 5 shown in FIG. 3 can be attached, said sealing element being attached in said groove 8 in a positively locking manner and in such a way that air cannot flow in behind it.

Figure 4:
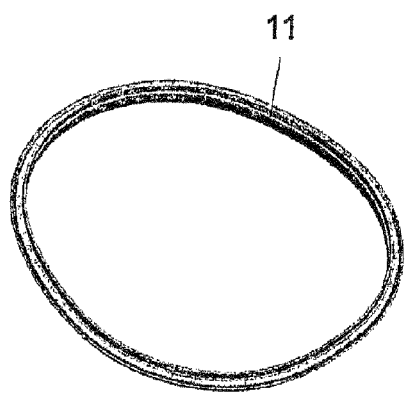
FIG. 4 is a perspective view of an embodiment of a retaining ring.

This connection is established by means of a ring 12 attached permanently and non-releasably to the sealing element 5, or by means of a retaining ring 11, as shown in FIG. 4, which consists of harder material.

Figure 5:
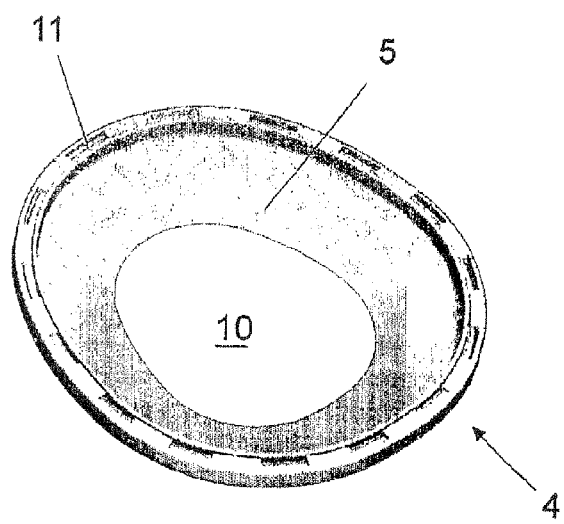
FIG. 5 is a perspective view of the overall device.

FIG. 5 shows the device as ultimately used in the circumferential groove 6 in the receiving sleeve. After first assembly, however, the functional part 3 remains in the groove 6 in the receiving sleeve 1, where it is fixed permanently, and only the sealing element 5 and the retaining ring 11 can be removed and, if appropriate, replaced.

The stump of the amputee is fitted into the limb receiving sleeve 1 in the known manner, largely centrally through the opening 10 in the sealing element 5.

In this case, the sealing element 5 rests on the stump or on the liner surrounding the stump, and seals it or the distal region of the receiving sleeve with respect to the atmosphere.

On further insertion of the stump into the sleeve, the wall thickness of the sealing element 5, which then increases the diameter of the stump at this point, can retract into a recess 9, shown in FIG. 1, on the inner side of the sleeve 1. A corresponding retraction space is also provided for the direct transition between the sealing element 5 and the receptacle 12, as a result of which the sealing element does not protrude when the stump is in its end position in the receiving sleeve. These measures effectively prevent the exertion of additional pressure by the sealing element 5 or the transition on the stump, and no additional circularly acting pressure, which would be physiologically disadvantageous, is exerted on the stump.

Figure 6:
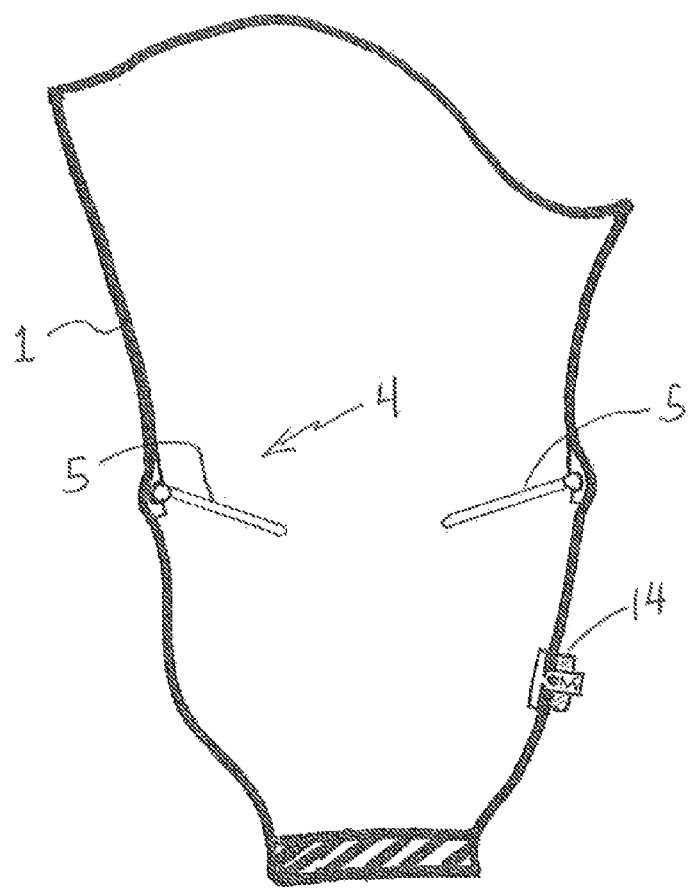
FIG. 6 is an illustration of a valve in the receiving sleeve for releasing air from the compartment.

FIG. 6 illustrates receiving sleeve 1 with complete device 4 and, valve 14 which allows air situated between the stump, the sealing element 5 and the stump receiving sleeve 1 to flow out when the stump is inserted into the at receiving sleeve 1, without air flowing into the volumetric compartment if there is a negative pressure there.

Figure 7:
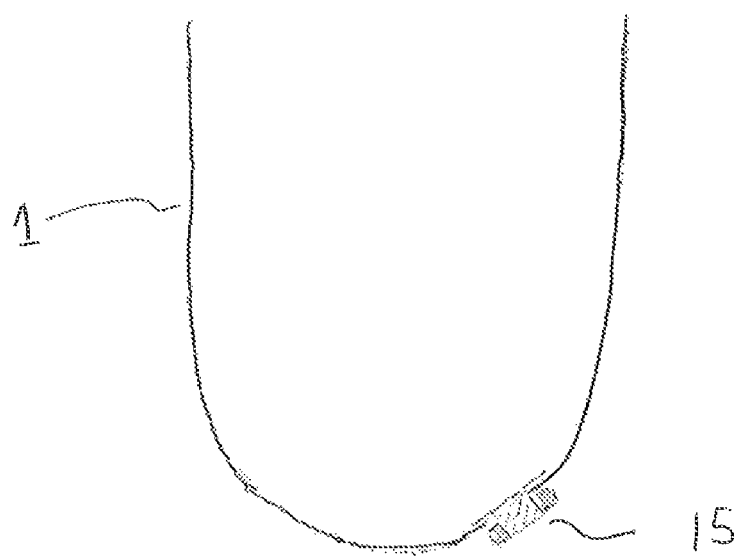
FIG. 7 is an illustration of a valve in the receiving sleeve for rear ventilating the compartment.

FIG. 7 illustrates a valve 15 which is integrated in a shaft and means of which the volumetric compartment can be rear-ventilated, in order to make is possible for the amputee to pull the stump back out of the stump receiving sleeve 1.

Now that preferred embodiments of the invention have been described in relation to the accompanying drawings, it should be noted that the invention is not restricted to these exact embodiments, and that various changes and modifications can be made thereto by a person skilled in the art, without departing from the scope of the invention as defined in the accompanying claims.

The invention claimed is:

1. A limb stump receiving sleeve comprising:
   an integratable locking device for locking a limb stump by sealing a distal region of an interior of the stump receiving sleeve with respect to the limb stump and surrounding atmosphere, wherein the locking device includes
   a functional element integrated in an inner face of the receiving sleeve, and
   an inwardly extending sealing element reversibly attached to said functional element in a positively locking manner and in such a way that air cannot flow in behind the sealing element, and
   a side of the functional element for inserting the sealing element which faces toward the interior of the stump receiving sleeve is circumferentially provided with a groove, in which the sealing element is reversibly attached in the positively locking manner such that air cannot flow in behind the sealing element.

2. The limb stump receiving sleeve as claiming in claim 1, wherein
   the functional element for attaching the sealing element is fixed non-releasably and in such a way that air cannot flow in behind the functional element in a groove in the receiving sleeve.

3. The limb stump receiving sleeve as claimed in claim 1, wherein
   the functional element for inserting the sealing element has an undercut for positively locking integration into a corresponding groove in the inner face of the receiving sleeve.

4. The limb stump receiving sleeve as claimed in claim 1, wherein,
   the stump receiving sleeve has a, recess situated distally from the functional element for at caching the sealing element.

5. The limb stump receiving sleeve as claimed in claim 1, wherein
   a center of the sealing element is surrounded by an opening, through which the limb stump can be inserted into the stump receiving sleeve.

6. The limb stump receiving sleeve as claimed in claim 1, wherein
   the sealing element consists of an elastomer material and a harder material, which is arranged circumferentially around the elastomer material, is joined thereto and by which the sealing element is reversibly attached to the groove in the functional element, which faces toward the interior of the stump receiving sleeve, in a positively locking manner and in such a way that air cannot flow in behind it.

7. The limb stump receiving sleeve as claimed in claim 1, and further comprising
   a valve, which allows air situated between the stump, the sealing element, and the stump receiving sleeve to flow out when the stump is being inserted, into the stump receiving sleeve, without air flowing into this volumetric compartment if there is a negative pressure there.

8. The limb stump receiving sleeve as claimed in claim 7, and further comprising a value which is integrated in a shaft and by means of which the volumetric compartment can be rear-ventilated, in order to make it possible for the amputee to pull the stump back out of the stump receiving sleeve.

9. The limb stump receiving sleeve as claimed in claim 1, wherein
   the sealing element has a non-adhering sliding property with respect to the surface of the liner around a stump.

* * * * *

UNITED STATES PATENT AND TRADEMARK OFFICE
CERTIFICATE OF CORRECTION

PATENT NO.        : 8,409,299 B2
APPLICATION NO.   : 12/936350
DATED             : April 2, 2013
INVENTOR(S)       : Christof Kurth It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 240 days.

Signed and Sealed this
First Day of September, 2015

Michelle K. Lee
*Director of the United States Patent and Trademark Office*